United States Patent [19]

Manabe

[11] Patent Number: 4,539,296
[45] Date of Patent: Sep. 3, 1985

[54] METHOD OF ANALYZING CHEMICAL SUBSTANCES

[75] Inventor: Sugio Manabe, Kodaira, Japan

[73] Assignee: Olympus Optical Co., Ltd., Japan

[21] Appl. No.: 550,507

[22] Filed: Nov. 10, 1983

Related U.S. Application Data

[63] Continuation of Ser. No. 312,961, Oct. 20, 1981, abandoned.

[30] Foreign Application Priority Data

Oct. 24, 1981 [JP] Japan .................................. 56-148135

[51] Int. Cl.³ .......................................... G01N 35/02
[52] U.S. Cl. ........................................ 436/47; 356/434; 356/435; 422/64; 422/67; 436/43; 436/164
[58] Field of Search ..................... 422/63–67; 356/434, 435; 436/43

[56] References Cited

U.S. PATENT DOCUMENTS

| | | | |
|---|---|---|---|
| 3,464,799 | 9/1969 | Kimbell | 422/91 |
| 3,975,727 | 8/1976 | Mader et al. | 356/435 |
| 4,276,051 | 6/1981 | Ginsberg et al. | 422/67 |
| 4,311,394 | 1/1982 | Manabe | 422/64 |
| 4,338,279 | 7/1982 | Orimo | 422/64 |

FOREIGN PATENT DOCUMENTS 55-87030 7/1980 Japan .
158580 7/1980 Japan .

Primary Examiner—Michael S. Marcus
Attorney, Agent, or Firm—Parkhurst & Oliff

[57] ABSTRACT

In a method of analyzing chemical substances in sample liquids, reagent blank absorbances with respect to a light amount transmitted through air or water are measured previously at a plurality of photometering positions and are stored in a memory. Then sample absorbances are measured at respective photometering positions and the reagent blank absorbances are substrated from the sample absorbances at the respective photometering positions, so that a required absorbance variation of the sample liquid with respect to time is calculated from the sample absorbances thus corrected. Therefore, even if a calibration curve linearity is not perfectly identical with each other at the respective photometering positions, it is possible to obtain accurate analyzing results.

6 Claims, 4 Drawing Figures

FIG_3
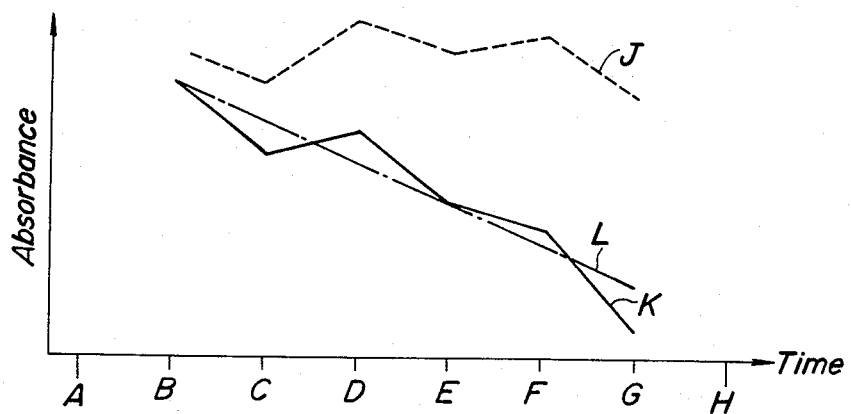
FIG_4
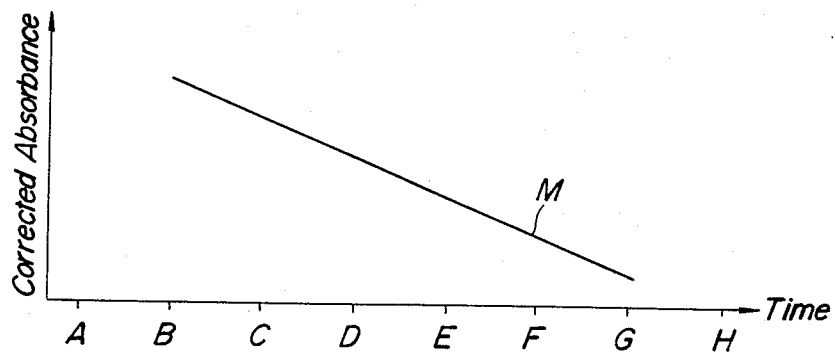

METHOD OF ANALYZING CHEMICAL SUBSTANCES

This a continuation of application Ser. No. 312,961 filed Oct. 20, 1981, now abandoned.

BACKGROUND OF THE INVENTION

The present invention relates generally to a technique for analyzing biochemical substances, and especially to an absorptiometric method for measuring existance, concentrations and/or activities of chemical substances in sample liquids in an accurate manner by measuring variations in absorbance with respect to time.

Such a method of measuring the concentrations or activities of substances contained in a sample by detecting a variation in absorbance or optical density of a test liquid which is a mixture of the sample and one or moe reagents is sometime called a kinetic assay and has been used for measuring enzymes such as Glumatate Oxalacetate Transaminase (GOT), Glumatate Pyruvate Transaminase (GPT), and the like. In a known apparatus for effecting such a kinetic assay, only one photometering position is arranged and the variation in absorbance is measured successively or intermittently while a cuvette containing the test liquid is kept stably at the photometering position for a given time period. Then concentrations and/or activities of chemical substances in sample liquid are calculated according to the measured variations of absorbance. However, in order to perform a highly precise analysis, it is necessary or advantageous to measure the large variation of absorbance. For this purpose it is necessary to keep respective samples at the photometering position for a sufficiently long time. Therefore, such analyzing apparatus has a slow feeding speed and thus, there is a drawback that a sample processing or treating ability is low.

In order to overcome such a drawback, there has been proposed an analyzing apparatus comprising a plurality of photometering positions aranged along a reaction line. While cuvettes containing test liquids which are mixtures of samples and reagents are fed along the reaction line continuously or intermittently, the absorbances of the test liquids are measured only once at respective photometering positions. Then, the variation in absorbance can be derived as a difference between absorbance values measured at any two photometering positions. In such an analyzing apparatus, since the sample absorbance is photometered at a plurality of photometering positions, it is not necessary to remain the cuvettes at the respective photometering positions for a long time and thus, the processing speed can be made high. However, in such a method, a plurality of measuring channels each belonging to respective photometering positions have different characteristics due to difference in various factors such as stray light, electrical characteristics of pre-amplifier, and deviation in light axis with respect to a cuvette position. These differences result in variation of linearity of calibration curve of respective photometering channels. Moreover, in the kinetic assay, since variations of absorbances of reagents with respect to time cause an error in analyzed results, it is necessary to compensate the absorbance variations of the reagents with respect to time.

Therefore, in such an analyzing apparatus, an analyzing operation has been usually performed according to the following steps;

(1) Adjustment of Apparatus at 0% and 100%.

(2) Measurement of Reagent Blank; the absorbance variation per unit time $\Delta E_B$ of the reagent blank liquid (reagent per se) is measured.

(3) Calculation of Concentration or Activity Converting Coefficient I; in one case the coefficient is calculated from an equation $I = V_t/(\epsilon \times d \times v_s)$, wherein $v_s$, $v_r$, d, and $\epsilon$ are sample amount, reagent amount, optical path length, and atomic absorption coefficient, respectively, and $V_t$ indicates $v_s + v_r$. In another case the absorbance variation per unit time $\Delta E_s$ is obtained by using a standard liquid or a controlling serum with known concentration (activity) c as the sample liquid and then the coefficient is calculated from an equation $I = c/(\Delta E_s \Delta E_B)$.

(4) Measurement of Unknown Sample; the absorbance variation per unit time $\Delta E_v$ is measured and then a measuring result i.e. a concentration $c_x$ of a substance to be measured is calculated from a formula $c_x = I \times (\Delta E_v \Delta E_b)$.

The reagent blank mentioned above is generally obtained by performing the photometry upon the reagent itself by a plurality of times on the basis of a light flux passing through air or water. In the analyzing apparatus having a plurality of measuring channels, at first, the reagent absorbance is measured at respective photometering positions by delivering only reagent into the cuvette on the basis of a transmittivity of air or water and then the reagent blank is calculated from a difference between the reagent absorbances measured at the different photometering position. In this case, if the linearity of calibration curves at respective photometering positions is not strictly identical with each other, it is not possible to obtain accurately the reagent blank from the difference between the reagent absorbances measured at different photometering positions. In order to overcome such a drawback, if the analysis is performed by measuring the absorbance variation with respect to time for all samples including the reagent blank at two fixedly predetermined photometering positions, it is possible to use the reagent blank as a difference in absorbance variation between these photometering positions, because in this case the difference in analyzing property between the phomometering positions maybe considered to be always constant. Then the reagent blank is stored in a memory and the absorbance differences of samples can be corrected by the stored reagent blank. However, in case of performing the analysis by selecting suitable absorbances measured at any two photometering positions, since the two photometering positions may be different for respective samples, it is necessary to store a very large number of absorbance variations as the reagent blanks. For instance, when an amount of substances to be measured is small, it is preferable to derive a difference in absorbance values measured at two photometering positions which are spaced farthest, but when an amount of substance is abnormally large, it is advantageous to calculate difference in absorbance values measured at two adjacent photometering positions. Further, even in case of using the absorbance values between adjacent photometering positions, measurement timings in the reaction procedure should be made different for respective samples. In order to satisfy such requirements, it is necessary to store a very large number of reagent blanks calculated from all differenes in absorbance values between all the photometering positions. For instance, when there are provided fifteen photometering positions along the reaction line, more than hundred reagent blanks have to be stored in the memory. Therefore, the memory is liable to be large and a control circuit for the memory becomes very complicated.

SUMMARY OF THE INVENTION

The present invention has for its object to provide a novel and useful method of analyzing chemical substances in sample liquids, which can obviate the above mentioned drawbacks of the known methods and can perform a highly accurate, reliable and speedy analysis even if measuring characteristics at respective photometering positions are not strictly identical with each other.

According to the invention, in a method of analyzing chemical substances in sample liquids by deriving an absorbance variation with respect to time of a test liquid which is a mixture of a sample and one or more reagents from absorbance values measured at a plurality of photometering positions and by calculating a concentration or an activity of one or more given chemical components in the sample liquid according to said absorbance variation with respect to time, the improvement comprises a step of detecting reagent blank absrobances at said plurality of photometering positions; a step of storing the detected reagent blank absorbances; a step of correcting sample absorbances measured at said respective photometric positions in accordance with said reagent blank absorbances; and a step of calculating said absorbance variation of said test liquid according to the sample absorbances thus corrected.

BRIEF DESCRIPTION OF THE DRAWINGS

FIGS. 3 and 4 are schematic diagrams explaining the operation of the chemical substance analyzing method according to the invention.

DESCRIPTION OF THE PREFERRED EMBODIMENTS

Figure 1:
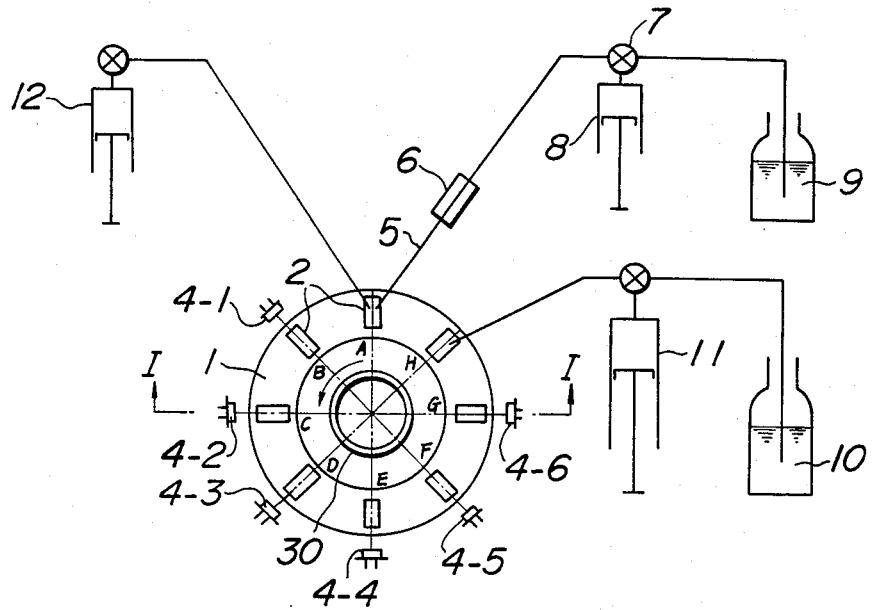
FIG. 1 is a schematic plan view showing an embodiment of an analyzing apparatus for carrying out the chemical substance analyzing method according to the invention.

FIG. 1 is a schematic plan view showing an embodiment of an analyzing apparatus for effecting the chemical substance analyzing method according to the invention. A plurality of cuvettes 2 are arranged on a turntable 1 as shown in FIG. 1 and the turntable 1 is rotated in a direction shown by an arrow continuously or intermittently. A sample and a reagent are delivered quantitatively into the cuvette 2 at a position A by means of delivering pumps 12 and 8, respectively, and then the absorbance is photometered successively at six positions B, C, D, E, F and G illustrated in FIG. 1. Light receiving elements 4-1 to 4-6 are arranged at these positions, at which a light flux transmitted through the sample liquid is received so as to obtain required data. Since delivering processes for sample, reagent, and washing liquid are same, the reagent delivery process will be explained as follows representatively. A reagent delivering pump 8 comprises a trigonal valve 7 so as to suck a reagent 9 in the delivering pump 8. Moreover, since the apparatus comprises a preheat portion 6, a sample liquid is preheated near a reaction temperature and is discharged into the cuvette 2 through a probe 5. Followingly at a position H the sample liquid in the cuvette 2 is discharged and then a washing liquid 10 is delivered into the cuvette 2 by means of a delivering pump 11 so as to wash the cuvette 2.

Figure 2:
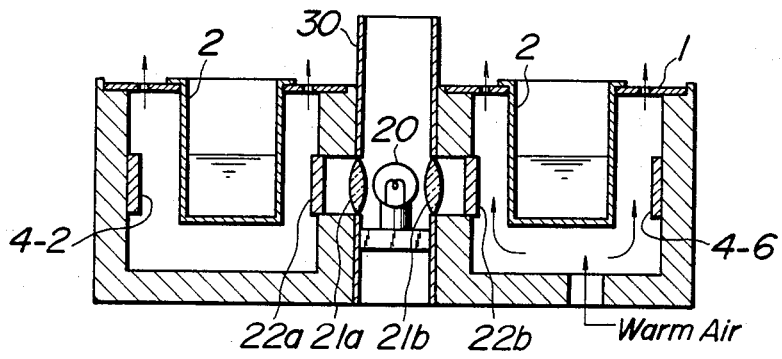
FIG. 2 is a cross-sectional view cut along a line I—I in FIG. 1.

FIG. 2 is a cross sectional view of the analyzing apparatus cut along a line I-I in FIG. 1. Each of the photometering positions B to G is composed of a lens (21a, 21b) arranged on a tube 30, a filter (22a, 22b) and a light receiving element 4-1 to 4-6. The light fluxes emitted from a lamp 20 arranged in the tube 30 are converaged into parallel light fluxes by means of the lenses 21a, 21b. Then the parallel light fluxes are transmitted through the filters 22a, 22b and the sample liquids onto the light receiving elements 4-2, 4-6 which produce electrical signals representing absorbances of test liquids in the cuvettes 2. Moreover, in order to keep the test liquids in the cuvettes 2 at a given desired temperature, a warm air is circulated through the apparatus.

FIGS. 3 and 4 are schematic diagrams explaining the operational principle of the chemical substance analyzing method according to the invention with reference to the analyzing apparatus shown in FIG. 1. In FIGS. 3 and 4 a vertical and a horizontal axes indicate an absorbance and a time, respectively. In an embodiment of the analyzing method according to the invention, the analysis is effected in the following analyzing steps.

(1) Adjustment of Apparatus at 0% and 100%

This is done in the same way as usual.

(2) Measurement of Reagent Blank

In this invention, the absorbance variation of the reagent blank per unit time is not measured, but absorbance values of the reagent blank at respective measuring positions B to G are measured with respect to air or water blank which is measured by supplying only air or water into the cuvette 2. The transmittivity of air or water is assumed to be 100%. In such a case, since the linearity of calibration curves at respective photometering positions is not perfectly identical with each other, the absorbance value of reagent blank at respective photometering positions fluctuate as shown by a borken line J in FIG. 3. The measured absorbances of the reagent blank are stored at predetermined memory positions.

(3) Calculation of Concentration or Activity Converting Coefficient I

In case of performing the measurement using the standard sample such as a control serum having a known concentration (activity) c, the absorbances of the standard sample are measured at respective photometering positions, and then differences between the thus detected absorbances and the absorbances of the reagent blank which have been stored at the respective photometering positions are obtained. The converting coefficient I is derived by calculating the absorbance variation per unit time from the corrected absorbances at the photometering positions.

(4) Measurement of Unknown Sample

If an unknown sample is measured successively at the photometering position B to G, the absorbances at respective photometering positions change as illustrated by a solid line K in FIG. 3. A chain line L in FIG. 3 indicates an expected absorbance variation of the same sample in case that all the photometering positions have the perfectly same characteristics. In this invention, at first differences between the sample absorbance measured at the respective photometering positions and the stored absorbances of reagent blank are obtained so as to correct the sample absorbances. Then the corrected absorbance variation of the sample can be represented by a solid line M in FIG. 4, and the absorbance variation of sample per unit time can be calculated by deriving a difference between the corrected absorbances at different photometering positions. Then the concentrations and activities of chemical substances can be obtained on the basis of the sample absorbance variation obtained from the aforesaid procedures.

According to the present invention mentioned above, since the absorbances of the reagent blank with respect to air or water at every photometering position, must be stored, a memory capacity increases a little. However, considering the improvements of the invention that a sample processing ability increases as mentioned above and that an accurate analysis can be performed even if the calibration curve linearity at respective photometric positions is not perfectly identical with each other, a little increase of the memory capacity is no problem.

In the embodiment mentioned above, the absorbance values of the reagent blank at the photometering positions are stored, but it is also possible to store absorbance values of a standard sample liquid having a previously known absorbance value at respective photometering positions.

As mentioned above in the present invention, even if a plurality of photometering positions have different characteristics, a percise analysis can be performed. It should be noted that in case of existing large difference between the absorbance of reagent blank and that of the sample, the difference between the photometeric characteristics at respective photometric positions becomes predominant, but this occurs for abnormally high concentration (high activity) sample, so that an error becomes relatively small. Moreover, since, at a range from an upper limit of normal value to near a boundary value which needs the highest accuracy, the absorbance variation is small and also a difference in absorbance between the samples and the reagent is small, the accurate analysis can be performed by effecting the correction for the respctive photometering positions according to the invention.

What is claimed is:

1. A method of analyzing chemical substances in a sample by deriving an absorbance variation with respect to time of a test liquid which is a mixture of a sample liquid and at least one known reagent comprising the step of:

delivering a reagent into a first container to form a reagent blank;
   moving the container containing the reagent successively through a plurality of photometric positions;
   measuring absorbances of the reagent blank at respective photometric positions;
   storing the measured absorbances of the reagent blank in a memory;
   delivering a standard test liquid which is a mixture of a standard sample having a known concentation c and the reagent into a second container;
   moving the second container containing the standard test liquid succesively through the plurality photometric positions;
   measuring absorbances of the standard test liquid at respective photometric positions;
   deriving differences between absorbances of the reagent blank measured at at least two photometric positions, and the absorbances of the standard test liquid measured at corresponding photometric positions to produce at least two corrected absorbances of the standard test liquid;
   deriving an absorbance variation per unit time from a difference between the corrected absorbances of the standard test liquid;
   calculating a converting coefficient I from said absorbance variation per unit time in the corrected absorbances of the standard test liquid and the known concentration c of the substances in the standard sample;
   storing the converting coefficient I thus calculated in the memory;
   delivering a test liquid into a third container;
   moving the third container containing the test liquid successively through the photometric positions;
   measuring absorbances of the test liquid at respective photometric positions;
   deriving differences between the absorbances of the reagent blank measured at at least two photometric positions and the absorbances of the test liquid measured at corresponding photometric positions to produce at least two corrected absorbances of the test liquid;
   deriving an absorbance variation per unit time from a difference between the corrected absorbances of the test liquid;
   calculating a concentration of the substances in the sample liquid from said absorbance variation per unit time in the absorbance of the test liquid and said converting coefficient I.

2. The method according to claim 1, wherein said absorbance variation per unit time in the absorbance of the standard sample liquid is derived by dividing said difference in the absorbances of the standard test liquid measured at said two photometric positions by a time period which is equal to a time difference between timings at which the measurements are effected at said two photometric position.

3. The method according to claim 1, wherein said absorbance variation per unit time in the absorbance of the sample liquid is derived by dividing said difference in the absorbances of the test liquid measured at said two photometric positions by a time period which is equal to a time difference between timings at which the measurements are effected at said two photometric positions.

4. The method according to claim 1, further comprising, prior to the measurement of the absorbances of the reagent blank, the steps of moving a fourth container containing medium having a transmittivity of 100% successively through the plurality of photometric positions each having means for photometering, and
   measuring absorbances of the fourth container containing said medium to adjust zero absorbance at respective photometric positions.

5. The method according to claim 4, wherein said medium having the transmittivity of 100% is water.

6. The method according to claim 4, wherein said medium having the transmittivity of 100% is air.

* * * * *